(12) United States Patent
Ushijima et al.

(10) Patent No.: US 11,717,502 B2
(45) Date of Patent: *Aug. 8, 2023

(54) BLOOD FLOW IMPROVER

(71) Applicant: WAKUNAGA PHARMACEUTICAL CO., LTD., Osaka (JP)

(72) Inventors: Mitsuyasu Ushijima, Akitakata (JP); Kayo Kunimura, Akitakata (JP); Yukihiro Kodera, Akitakata (JP); Naoaki Morihara, Akitakata (JP)

(73) Assignee: WAKUNAGA PHARMACEUTICAL CO., LTD., Osaka (JP)

( * ) Notice: Subject to any disclaimer, the term of this patent is extended or adjusted under 35 U.S.C. 154(b) by 142 days.

This patent is subject to a terminal disclaimer.

(21) Appl. No.: 16/632,036

(22) PCT Filed: Aug. 6, 2018

(86) PCT No.: PCT/JP2018/029386
§ 371 (c)(1),
(2) Date: Jan. 17, 2020

(87) PCT Pub. No.: WO2019/031442
PCT Pub. Date: Feb. 14, 2019

(65) Prior Publication Data
US 2020/0147021 A1 May 14, 2020

(30) Foreign Application Priority Data
Aug. 7, 2017 (JP) ................ 2017-152366

(51) Int. Cl.
*A61K 31/198* (2006.01)
*A23L 33/10* (2016.01)
*A61P 9/12* (2006.01)
*A61K 36/8962* (2006.01)

(52) U.S. Cl.
CPC ............ *A61K 31/198* (2013.01); *A23L 33/10* (2016.08); *A61K 36/8962* (2013.01); *A61P 9/12* (2018.01); *A61K 2236/33* (2013.01)

(58) Field of Classification Search
None
See application file for complete search history.

(56) References Cited

U.S. PATENT DOCUMENTS 10,363,234 B2 * 7/2019 Ushijima ............ A61K 31/198
2017/0360731 A1 12/2017 Suzuki et al.
2018/0147170 A1 5/2018 Ushijima et al.

FOREIGN PATENT DOCUMENTS

| JP | 5-60447 B2 | 9/1993 |
| JP | 4255138 B2 | 4/2009 |
| KR | 10-2017-0041568 A | 4/2017 |
| WO | WO 2016/088892 A1 | 6/2016 |
| WO | WO 2016/199885 A1 | 12/2016 |

OTHER PUBLICATIONS

Matsutomo, et al., The Journal of Nutrition, 146:450S. (Year: 2016).*
Moriguchi, et al., The Journal of Nutrition, 131:1016S. (Year: 2001).*
Matsutomo, et al., The Journal of Nutrition, Supplement-2014 International Garlic Symposium: Role of Garlic in Cardiovascular Disease Prevention, Metabolic Syndrome, and Immunology, 450S-455S. (Year: 2016).*
Matsutomo, et al., Journal of Chromatography B, 1046:147. (Year: 2017).*
International Search Report dated Sep. 18, 2018 in PCT/JP2018/029386 filed on Aug. 6, 2018, 2 pages.
"Ninniku no Kagaku (in Japanese, The Science of Garlic)," Asakura Publishing Co., Ltd., 2000, p. 93-122, 32 total pages (with partial English translation).
Nakagawa, S. et al., "Prevention of Liver Damage by Aged Garlic Extract and Its Components in Mice," Phytotherapy Research, vol. 3, No. 2, 1989, pp. 50-53.
Hatono, S. et al., "Chemopreventive effect of S-allylcysteine and its relationship to the detoxification enzyme glutathione S-transferase," Carcinogenesis, vol. 17, No. 5, 1996, pp. 1041-1044.
Cruz, C. et al., "Renoprotective and antihypertensive effects of S-allylcysteine in 5/6 nephrectomized rats," Am. J. Physiol. Renal Physiol., vol. 293, 2007, pp. F1691-F1698.
Okuhara, T. "Clinical review on peripheral circulation of GE," Jpn. Pharmacol. Ther., vol. 22, No. 8, 1994, pp. 335-341, 8 total pages (with partial English translation).
Anim-Nyame, N. et al., "Garlic supplementation increases peripheral blood flow: a role for interleukin-6?" Journal of Nutritional Biochemistry, vol. 15, 2004, pp. 30-36.
Kodera, Y. et al., "Chemical and Biological Properties of S-1-Propenyl-L-Cysteine in Aged Garlic Extract," Molecules, vol. 22, 2017, pp. 1-18.
Ushijima, M. et al., "Effects of S-1-propenylcysteine, a sulfur compound in aged garlic extract, on blood pressure and peripheral circulation in spontaneously hypertensive rats," Journal of Pharmacy and Pharmacology, vol. 70, 2018, pp. 559-565.
Japanese Office Action dated Jul. 12, 2022, in Japanese Patent Application No. 2019-535642 (with English Translation).
Web page of Daiichi Yakuhin Kogyo Co., Ltd. (wayback machine archive), "Blood circulation and hypertension", 1-4, [online], Mar. 27, 2016 <URL:http://web.archive.org/web/20160527024832/https://www.toyama kusuri.jp/ja/members/lectures/document/kouketsuatsu/kouketsuatsu.pdf, pp. 1-4 (with a partial machine translation).
Office Action dated Sep. 5, 2022, in corresponding European Patent Application No. 18844716.3, 11 pages.
Tianyi Wang, et al., "Determination of Hiesho among Young Japanese Females using Thermographic Technique", Advanced Biomedical Engineering, vol. 10, Jan. 1, 2021, pp. 11-17, XP055952100, doi:10.14326/abe.10.11.

(Continued)

*Primary Examiner* — Michael Barker
(74) *Attorney, Agent, or Firm* — Oblon, McClelland, Maier & Neustadt, L.L.P.

(57) ABSTRACT

Provided is a blood flow improver which is safe and has a mild action. The blood flow improver comprises S-1-propenylcysteine or a salt thereof as an active ingredient.

9 Claims, No Drawings

(56) References Cited

OTHER PUBLICATIONS

Kaori Kono, et al., "Vascular Endothelial Dysfunction and Autonomic Nervous Hyperactivity among Premenopausal Women with Cold-Sensitivity Constitution (Hiesho)", The Tohoku Journal of Experimental Medicine, vol. 253, No. 1, Jan. 1, 2021, pp. 51-60, XP055952101, doi:10.1620/tjem.253.51.

Kwang-Ho Bae, et al., "The association between cold hypersensitivity in the hands and feet and chronic disease: results of a multicentre study", BMC Complementary and Alternative Medicine, vol. 18, No. 1, Jan. 31, 2018, pp. 1-8, XP021253213.

Yoichi Iizuka, et al., "Characteristics of neck and shoulder pain (called katakori in Japanese) among members of the nursing staff", Journal of Orthopaedic Science, vol. 17, No. 1, Nov. 18, 2011, pp. 46-50, XP035007044.

Jian-Guo Bau, et al., "Correlations of Neck/Shoulder Perfusion Characteristics and Pain Symptoms of the Female Office Workers with Sedentary Lifestyle", Plos One, vol. 12, No. 1, Jan. 6, 2017, p. e0169318, XP055952104, doi:10.1371/journal.pone.0169318.

Francisco Selva-Sarzo, et al., "The Direct Effect of Magnetic Tape® on Pain and Lower-Extremity Blood Flow in Subjects with Low-Back Pain: A Randomized Clinical Trial", Sensors, vol. 21, No. 19, Sep. 29, 2021, 6517, pp. 1-12, XP055952118, doi:10.3390/s21196517.

* cited by examiner

BLOOD FLOW IMPROVER

TECHNICAL FIELD

The present invention relates to a blood flow improver.

BACKGROUND ART

Blood has a transport function, an immune function, a hemostatic function, and a homeostasis-maintaining function. The transport function is a function for delivering water, oxygen, nutrient, hormone, and heat to cells all over the body, and for collecting carbon dioxide and waste products output from the cells. Systemic blood circulation requires normal functions of heart and blood vessels. Coldness or nervousness, however, causes peripheral vasoconstriction, which results in obstruction of blood flow and various abnormalities.

For example, cold sensitivity develops when sympathetic nerve prevails due to lowered temperature or hormonal imbalance and blood vessels of limbs are constricted. Stiff shoulder is said to be a result of stiffness of muscle around shoulders, which leads to obstruction of blood flow and accumulation of waste products, and causes inflammation or pain. It is therefore important for treatment of cold sensitivity or stiff shoulder to warm the affected area to improve the blood circulation.

Garlic contains γ-glutamyl-S-allylcysteine as its unique ingredient. Upon cutting, crushing, grating, or aging of garlic, the ingredient is converted by an enzyme called as γ-glutamyl transpeptidase contained in garlic, into water-soluble S-allylcysteine (abbreviated as SAC, hereinafter). Water-soluble compounds, other than SAC, produced as a result of such enzymatic reaction include S-methyl cysteine (abbreviated as SMC, hereinafter), and S-1-propenylcysteine (abbreviated as S1PC, hereinafter) (Non Patent Literature 1).

It has been reported that SAC has a variety of pharmacological effects including a preventive effect on hepatopathy (Non Patent Literature 2, Patent Literature 1), a preventive effect on colorectal cancer (Non Patent Literature 3), and a hypotensive effect (Non Patent Literature 4). Also, it has been reported that SMC has a preventive effect on hepatopathy (Patent Literature 1) and an improving effect on brain disease (Patent Literature 2).

It has been reported that S1PC has an immune-modulating function (Patent Literature 3), and a hypotensive effect (Patent Literature 4), but not reported that it has an improving effect on blood circulation.

CITATION LIST

Patent Literature

Patent Literature 1: JP 05-060447 B
Patent Literature 2: JP 4255138 B2
Patent Literature 3: WO 2016/088892 A
Patent Literature 4: WO 2016/199885 A

Non Patent Literature

Non Patent Literature 1: "Ninniku no Kagaku (in Japanese, The Science of Garlic)", 1st Ed. Published by Asakura Publishing Co., Ltd., p. 93-122, 2000.
Non Patent Literature 2: Phytother Res. 3:50-53, 1989.
Non Patent Literature 3: Carcinogenesis, 17(5):1041-1044, 1996
Non Patent Literature 4: Am. J. Physiol. Renal Physiol., 293:F1691-F1698, 2007.

SUMMARY OF INVENTION

Technical Problem

The present invention relates to a provision of a blood flow improver that has few side effects and has a mild action.

Solution to Problem

The present inventors have variously studied on utility of S1PC or a salt thereof, and found that S1PC or a salt thereof has an excellent improving effect on blood flow, and is useful as a blood flow improver. Then, they have completed the present invention.

That is, the present invention relates to 1) to 11) below.

1) A blood flow improver comprising S1PC or a salt thereof as an active ingredient;
2) The blood flow improver according to 1), in which the blood flow improver prevents or improves cold sensitivity, stiff shoulder, backache or swelling;
3) The blood flow improver according to 1) or 2), in which the rate of trans isomer in the S1PC is from 50 to 100% when the total of trans isomer and cis isomer is 100%;
4) The blood flow improver according to any one of 1) to 3), in which the S1PC or a salt thereof is derived from at least one Allium plant selected from the group consisting of garlic, onion, elephant garlic, Chinese chive, and spring onion;
5) The blood flow improver according to 4), in which the S1PC or a salt thereof is obtained by extracting the Allium plant in a 10 to 50% aqueous ethanol solution at 0 to 80° C. for one month or longer, adsorbing the obtained extract to a cation exchange resin, eluting the adsorbate with a 0.1 to 3 N ammonia water, subjecting the eluate to a silica gel column chromatography and/or reverse phase column chromatography, and collecting the resulting;
6) The blood flow improver according to any one of 1) to 5), in which the blood flow improver is a medicine.
7) The blood flow improver according to any one of 1) to 5), in which the blood flow improver is a food.
8) A food for improving blood flow comprising S1PC or a salt thereof as an active ingredient.
9) Use of S1PC or a salt thereof, for manufacturing a blood flow improver.
10) S1PC or a salt thereof for use in improvement of blood flow.
11) A method of improving blood flow comprising administrating S1PC or a salt thereof.

Advantageous Effects of Invention

An excellent effect of improving blood flow is observed in S1PC or a salt thereof, which is an active ingredient of the blood flow improver of the present invention. Such effect of improving blood flow is expected to relieve muscle fatigue, muscle pain, stiff shoulder, stiff muscle, backache, joint pain, and nerve pain, in addition to cold sensitivity and chilblains. The active ingredient is a compound contained in plants which have been eaten for years, so that the ingredient per se is highly safe. Hence, the present invention can provide a material which is highly safe even if administered over a long period, and is applicable to prevention and treatment of various diseases in association with obstruction of blood flow.

DESCRIPTION OF EMBODIMENTS

In the present invention, S1PC is a cysteine derivative represented by formula (1) below.

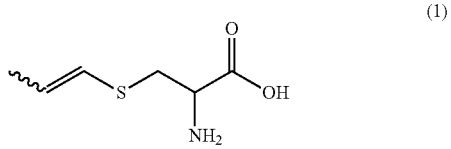

(1)

This compound has a cis or trans configuration as indicated by a wavy line in formula (1), and the rate of the trans isomer is preferably high. When the total of the trans isomer and the cis isomer is 100%, the rate of the trans isomer preferably is from 50 to 100%, more preferably from 75 to 100%, even more preferably from 80 to 100%, and even more preferably from 90 to 100%.

An asymmetric carbon can also exist in the cysteine structure, and an optical isomer is present therein and may be in any of D form, L form, or racemic form.

The salt of S1PC may be either an acid addition salt or a base addition salt. Examples of the acid addition salt include (a) salts with mineral acids such as hydrochloric acid, sulfuric acid, nitric acid, and phosphoric acid; (b) salts with organic carboxylic acids such as formic acid, acetic acid, citric acid, fumaric acid, gluconic acid, malic acid, succinic acid, tartaric acid, trichloroacetic acid, and trifluoroacetic acid; and (c) salts with sulfonic acids such as methanesulfonic acid, benzenesulfonic acid, p-toluenesulfonic acid, mesitylenesulfonic acid, and naphthalenesulfonic acid. Further, examples of the base addition salt include (a) salts with alkali metals such as sodium and potassium; (b) salts with alkaline earth metals such as calcium and magnesium; (c) ammonium salts; and (d) salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenetylamine, 1-ephenamine, and N,N'-dibenzylethylenediamine.

S1PC or a salt thereof can exist not only in an unsolvated form, but also in the form of hydrate or solvate. Such hydrate or solvate can exist as any crystal form depending on conditions of manufacturing. Hence, S1PC or a salt thereof in the present invention encompasses all stereoisomers, hydrates, and solvates, and encompasses all polymorphic crystal forms or amorphous forms.

S1PC or a salt thereof in the present invention can be obtained by any of organic synthetic methods [1] H Nishimura, A Mizuguchi, J Mizutani, Stereoselective synthesis of S-(trans-prop-1-enyl)-cysteine sulphoxide. Tetrahedron Letter, 1975, 37, 3201-3202; 2] J C Namyslo, C Stanitzek, A palladium-catalyzed synthesis of isoalliin, the main cysteine sulfoxide in Onion (Allium cepa). Synthesis, 2006, 20, 3367-3369; 3] S Lee, J N Kim, D H Choung, H K Lee, Facile synthesis of trans-S-1-propenyl-L-cysteine sulfoxide (isoalliin) in onions (Allium cepa). Bull. Korean Chem. Soc., 2011, 32(1), 319-320]; biochemical methods using enzymes or microbes; or methods combining these methods. In addition to these methods, S1PC or a salt thereof may be obtained by extraction and purification from plants that contain the compounds, such as an Allium plant, or processed products thereof.

Hence, S1PC or a salt thereof of the present invention may be not only an isolated and purified product, but also a crude product, or a fraction in which the content of S1PC or a salt thereof has been increased by extraction from the plants.

Here, examples of the Allium plant that contains S1PC or a salt thereof include garlic (Allium sativum L.), onion (Allium cepa L.), elephant garlic (Allium ampeloprasum L.), Chinese chive (Allium tuberosum. Rottl. Ex K. Spreng.), and spring onion (Allium fistulosum L.). These plants may be used alone, or in combination. Further, the Allium plants may be used fresh as they are, or may be used after removing their outer skins if necessary, and then cutting or shredding. Moreover, they may be dried by, for example, freeze-drying or hot-air-drying, or may be powdered.

When a fraction extracted from the Allium plant is used as S1PC or a salt thereof in the present invention, the fraction may be obtained, for example, by 1) extracting the Allium plant in a 10 to 50% aqueous ethanol solution at 0 to 80° C. for one month or longer, and 2) subjecting the obtained extract to solid-liquid separation, and then collecting a fraction extracted with the aqueous ethanol solution.

The aqueous ethanol solution used in step 1) may be a 10 to 50% aqueous ethanol solution, and is preferably an aqueous ethanol solution having an ethanol concentration of 20 to 40%. The treatment temperature may be set to a range from 0 to 80° C., preferably from 10 to 60° C., and more preferably from 20 to 40° C. The duration of extraction treatment under the above condition is at least one month, preferably from 1 to 20 months, and more preferably from 1 to 10 months. Taking into consideration of, for example, sanitation and volatility of ethanol, the present step may be performed in an airtight state, in a hermitically sealed state or in a closed container. It is preferred to use the closed container.

In step 2), the extract obtained in step 1) may be subjected to solid-liquid separation, and then a fraction extracted with the aqueous ethanol solution is collected. The collected product is concentrated as appropriate so that an extract fraction that contains S1PC or a salt thereof can be obtained. The extract fraction may be used directly, or may be used after being appropriately dried by spray drying, for example.

Further, S1PC or a salt thereof can be isolated from the extract fraction that contains such S1PC or a salt thereof, by combining a dialysis method using a dialysis membrane with a molecular exclusion size of 3000 to 4000, if necessary, an adsorption/separation method using a cation exchange resin, and a separation/purification method based on normal phase chromatography or reverse phase chromatography.

Here, examples of the adsorption/separation method using a cation exchange resin include a method of adsorbing S1PC or a salt thereof to a cation exchange resin e.g., Amberlite (from Dow Chemical Company), DOWEX (from Dow Chemical Company), DIAION (from Mitsubishi Chemical Corporation)), and eluting it with a 0.1 to 3 N ammonia water.

Examples of the normal phase chromatography include a method of using a silica gel column and eluting it with a chloroform/methanol/water mixture.

Examples of the reverse phase chromatography include a method of using an octadecylsilyl column and eluting it with a 0.01 to 3% aqueous formic acid solution.

Preferably, there is a method including the steps of: dialyzing the above fraction extracted with aqueous ethanol solution (dialysis membrane: molecular exclusion size=3000 to 4000), adsorbing the resultant to a cation exchange resin, eluting the adsorbate with a 0.5 to 2 N ammonia water, subjecting the eluate to silica gel column chromatography (solvent: a chloroform/methanol/water mixture) to collect a fraction that contains the target substance, and then further subjecting the fraction to reverse phase column chromatography for fractionation (solvent: a 0.1 to 0.5% aqueous formic acid solution) to collect the target substance.

When the total of trans isomer and cis isomer is 100%, the rate of the trans isomer in the thus obtained S1PC is more preferably 50 to 100%, even more preferably 60 to 100%, and even more preferably 70 to 100%.

Generally, S1PC or a salt thereof in the present invention has low toxicity, since, for example, the $LD_{50}$ value of a diluted ethanol extract of garlic, as one of raw materials (extracted component: 14.5%, alcohol number: 1.18) is 50 ml/Kg or higher in each of the oral, intra-abdominal, and subcutaneous administration routes (The Journal of Toxicological Sciences, 9, 57(1984)), and Allium plants, including garlic and onion, have been commonly used as foods.

As shown in Examples, S1PC or a salt thereof has an excellent effect of improving blood flow. Hence, S1PC or a salt thereof can be a blood flow improver, and can be used for preventing or improving symptoms or diseases caused by obstruction of blood flow, such as cold sensitivity, stiff shoulder, backache, and swelling.

In the present invention, "improvement of blood flow" means change for the better or relief of stagnation of blood flow (obstruction of blood flow).

The blood flow improver of the present invention may be a medicine or food that exerts an effect of improving blood flow, or may be a material or formulation which is added thereto.

Further, the food encompasses a food which has a concept of use for improving blood flow and which is labeled with the concept, if necessary, a functional food, a food for patients, a food for specified health use, and a supplement.

The dosage form of a medicine that contains S1PC or a salt thereof of the present invention is not particularly limited and various dosage forms may be used. Preferred dosage form is a dosage form suitable for oral administration. Specific examples of the dosage form of formulation for oral administration include solid formulations such as tablets, capsules, fine granules, pills, and granules; and liquid formulations such as emulsions, solutions, suspensions, and syrups. Such medical formulations can be prepared by appropriately combining, for example, an excipient, a binder, a disintegrant, a lubricant, a colorant, a corrigent, and a pH adjuster with S1PC or a salt thereof of the present invention, if necessary in accordance with an ordinary method.

The form of a food that contains S1PC or a salt thereof of the present invention is not particularly limited. For example, the food may be in the form of various food compositions such as a solid foods, semiliquid foods, gelled foods, tablets, caplets, and capsules, and specifically may be in the form of various foods such as sweets, beverage, seasoning agent, processed sea foods, processed meat foods, bread, and health foods.

The foods can be produced by appropriately blending food materials used to usually produce these foods with S1PC or a salt thereof of the present invention in accordance with an ordinary method.

The above medicine or food, may further contain other substances having a blood flow improving action, e.g., vitamins such as vitamin E, vitamin C, and nicotinic acid; herbal medicines such as ginseng, ginger, capsicum, Japanese Zanthoxylum peel, pepper, garlic, Rehmannia root, peony root, Cnidium rhizome, Japanese Angelica root, peach kernel, moutan bark, safflower, and *Panax notoginseng*; fatty acids such as DHA and EPA; amino acids such as arginine and citrulline; prostaglandin E1 and prostaglandin 12; and other compounds and herbal medicines having phosphodiesterase-inhibiting action or peripheral vasodilatory action.

S1PC or a salt thereof is highly safe, so that the user can feel easy to take the aforementioned medicine and food for its daily health. Daily dose of the medicine or food may vary depending on a subject who ingests the medicine or food, ingestion form, types of materials and additives to be simultaneously ingested, and intervals of ingestion. Usually, the daily dose in terms of S1PC or a salt thereof is preferably from 0.001 to 10 mg/kg per day, and more preferably from 0.01 to 1 mg/kg. The daily dose may be divided into two to four intakes if desired.

EXAMPLES

Production Example 1

Production of S1PC-Containing Plant Extract Fraction (1) Garlic Extract Fraction with Aqueous Ethanol Solution Approximately 1 kg of peeled garlic bulbs and approximately 1000 mL of 30% ethanol were placed in a container, and closed. This container was allowed to stand at room temperature for one to ten months, with appropriate stirring. The mixture was then separated into a solid and a liquid, and the liquid was concentrated in vacuo to obtain a yellowish brown powder.

(2) Onion Extract Fraction with Aqueous Ethanol Solution

Peeled onions were each cut into two to four pieces. Approximately 5 kg of such pieces and approximately 5000 mL of 34% ethanol were placed in a container, and closed. This container was allowed to stand at room temperature for one to ten months, with appropriate stirring. The mixture was then separated into a solid and a liquid, and the liquid was concentrated vacuo.

(3) Chinese Chive Extract Fraction with Aqueous Ethanol Solution

Washed Chinese chive was cut to approximately 5 to 10 cm length. Approximately 5 kg of such Chinese chive and approximately 5000 mL of 34% ethanol were placed in a container, and closed. This container was allowed to stand at room temperature for one to ten months, with appropriate stirring. The mixture was then separated into a solid and a liquid, and the liquid was concentrated vacuo.

Production Example 2

Isolation of S1PC from Garlic Extract Fraction with Aqueous Ethanol Solution (1) The garlic extract fraction with aqueous ethanol solution obtained in Production Example 1(1) was placed in a dialysis tube with a pore size of 3500, and dialyzed against purified water. The external dialysis solution was passed through a cation exchange resin Dowex 50 W×8 (H+), and the resin was thoroughly washed with purified water. Amino acids adsorbed to the resin were eluted with 2 N ammonia, and concentrated in vacuo. The condensate was placed in a silica gel column, followed by column chromatography using a chloroform/methanol/water mixture as a solvent. The fractions containing a target substance (S1PC) were collected, and then concentrated. The concentrate was dissolved in water, and chromatographed on a reverse phase column for fractionation (octadecylsilyl column), using 0.1% formic acid as a solvent. The target substance was collected, and the solvent was removed by freeze-drying. The obtained freeze-dried substance was compared with the spectrum obtained from the standard substances whose structures are shown below using an NMR (solvent: deuterium oxide) and a mass spectrometer, and was confirmed to be a mixture of trans-S1PC and cis-S1PC (trans:cis=8:2)

Trans-S-1-Propenylcysteine

1H-NMR (500 MHz, in D2O-NaOD, δ): 1.76 (d, 3H, J=7.0 Hz), 2.98 (dd, 1H, J=7.5, 14.5 Hz), 3.14 (dd, 1H, J=4.5, 14.5 Hz), 3.69 (dd, 1H, J=4.5, 7.5 Hz), 5.10-5.14 (m, 1H), 6.02 (d, 1H, J=15.5 Hz);

13C-NMR (125 MHz, in D2O-NaOD, δ): 17.61, 33.53, 53.70, 119.92, 132.12, 172.73.

HRMS: observed [M+H]+=162.0583, calculated [M+H]+=162.0581

Cis-S-1-Propenylcysteine

1H-NMR (500 MHz, in D2O, δ): 1.74 (d, 3H, J=7.0 Hz), 3.21 (dd, 1H, J=7.5, 15.0 Hz), 3.31 (dd, 1H, J=4.5, 15.0 Hz), 3.95 (dd, 1H, J=4.5, 7.5 Hz), 5.82-5.86 (m, 1H), 6.01 (d, 1H, J=9.5 Hz);

13C-NMR (125 MHz, in D2O-NaOD, δ): 13.89, 33.88, 54.16, 122.58, 127.78, 172.63.

HRMS: observed [M+H]+=162.0580, calculated [M+H]+=162.0581

(2) Measurement of S1PC in Garlic Extract Fraction with Aqueous Ethanol Solution 500 mg to 1 g of the garlic extract fraction with aqueous ethanol solution obtained in Production Example 1(1) was transferred into a container, a 20 mM hydrochloric acid solution of S-n-3-butenylcysteine as an internal standard was added thereto, and the resultant solution was brought up to 20 mL with 20 mM hydrochloric acid. After stirring the resulting mixture well, a portion thereof was taken out and then centrifuged at 1750 G for approximately 10 minutes. A portion of the thus obtained supernatant was taken out, and then subjected to centrifugal filtration (at 15000 rpm for 10 minutes) using a centrifugal filtration unit (Amicon Ultra, cutoff: 3000). 20 µL of the filtrate was taken out, and derivatized using an AccQ-Tag Derivatization Kit (Waters). A standard compound was separately dissolved in 20 mM hydrochloric acid, and subjected to the same operation as the sample to prepare a standard solution for calibration curve. The sample solution and the standard solution were subjected to chromatography with Acquity UPLC system (Waters), and the content was determined. As a result, S1PC was a dry product (3.7±0.3 mg/g).

Test Example 1

Action of S1PC Against Decrease in Tail Skin Blood Flow in Water Immersion Stressed Rate
1. Method
1) Test Animals
Eight-week-old male Wistar rats purchased from Japan SLC, Inc. (Hamamatsu City) were grouped by nines, and preliminarily bred for two weeks. During preliminary breeding, handling was performed on the rats, and the rats were bred in a constant environment at a temperature of 23±1° C., a humidity of 50±10%, and a light/dark cycle of 12 hours (light period: 7 to 19 o'clock), and freely fed with artificial diet (CE-2, from CLEA Japan, inc.) and sterilized tap water.

2) Administration Experiment

The administration was performed by forced oral administration using a disposable feeding needle, and the fluid volume to be administered was 10 mL per kilogram of body weight of rat. As a sample to be administered, approximately 15 mg of S1PC (a cis/trans mixture) manufactured in Production Example 2 was precisely weighed, and dissolved in 15 mL of purified water. This solution was used as a stock solution. The solution was properly diluted to give 6.5 mg/kg (body weight of rat) of dosage and the diluted solution was orally administered to each rat a single time. To each rat of a control group, a solvent (purified water) was orally administered in the same manner as described above.

3) Water Immersion Stress and Measurement of Blood Flow

The rats were allowed to stand still in a room conditioned at a temperature of 20±0.5° C. for 30 minutes or longer, and attached with a probe for blood flow measurement using a binding tape at a position 5 cm away from the base of tail under isoflurane anesthesia. The blood flow was measured for 5 minutes using a laser tissue blood flowmeter (FLO-C1, from Omegawave Inc.). Average blood flow for 3 minutes during which the stable blood flow was shown was determined as the tail skin blood flow of the individual. The blood flow before water immersion was measured, and then S1PC or purified water was orally administered to the rats. Two hours after the administration, the rats were immersed up to the xiphoid and below in water at 15° C. for 10 minutes, using a stainless-steel restraint cage. The tail skin blood flow after the water immersion stress was measured one hour after the end of water immersion stress.

2. Results

Results are summarized in Table 1. Measured values were given as average±standard error.

Indications # and ## in Table 1 represent that significant differences (#; $p<0.05$, ##; $p<0.01$) were observed in the blood flow one hour after the end of water immersion stress with respect to the blood flow before water immersion, as a result of comparing them in the S1PC group and control group. Indication * represents that a significant difference (*; $p<0.05$) was observed in the S1PC group with respect to the control group, as a result of comparing them at each measurement time point. The t-test was used for examination.

TABLE 1

| | | Tail skin blood flow (mL/min/100 g) | |
| --- | --- | --- | --- |
| Test Solution | Dose (mg/kg) | Before water immersion stress | One hour after end of water immersion stress |
| Control group (purified water) | 0 | 2.81 ± 0.14 | 1.70 ± 0.14## |
| S1PC | 6.5 | 2.76 ± 0.15 | 2.21 + 0.15*# |

*$p < 0.05$ comparison with control group,
$p < 0.05$,
$p < 0.01$ comparison with blood flow before water immersion stress In the group treated with S1PC by single oral administration two hours before the water immersion stress, it was shown that, the degree of decrease in tail skin blood flow due to water immersion stress is smaller as compared with the control group, and a significant effect of improving the tail skin blood flow with respect to the control group was provided.

Test Example 2

Actions against Depressed Tail Subcutaneous Blood Flow in Water Immersion Stressed Rats, Compared between S1PC and SAC 1. Method 1) Test Animals Seven-week-old male Wistar rats purchased from Japan SLC, Inc. (Hamamatsu City) were grouped by twelves, and preliminarily bred for two weeks. During preliminary breeding, handling was performed on the rats, and the rats were bred in a constant environment at a temperature of $23\pm1°$ C., a humidity of $50\pm10\%$, and a light/dark cycle of 12 hours (light period: 7 to 19 o'clock), and freely fed with artificial diet (CE-2, from CLEA Japan, inc.) and sterilized tap water.

2) Administration Experiment

The administration was performed by forced oral administration using a disposable feeding needle, and the fluid volume to be administered was 10 mL per kilogram of body weight of rat. As a sample to be administered, approximately 15 mg each of S1PC (a cis/trans mixture) manufactured in Production Example 2 and SAC were precisely weighed, and dissolved in 15 mL of purified water. These solutions were used as a stock solution. The solutions were properly diluted to give 6.5 mg/kg (body weight of rat) of dosage and the diluted solution was orally administered to each rat a single time. To each rat of a control group, a solvent (purified water) was orally administered in the same manner as described above.

3) Water Immersion Stress and Measurement of Blood Flow

The rats were allowed to stand still in a room conditioned at a temperature of $20\pm0.5°$ C. for 30 minutes or longer, and attached with a probe for blood flow measurement using a binding tape at a position 5 cm away from the base of tail under isoflurane anesthesia. The blood flow was measured for 5 minutes using a laser tissue blood flowmeter (FLO-C1, from Omegawave Inc.). Average blood flow for 3 minutes during which the stable blood flow was shown was determined as the tail skin blood flow of the individuals. The blood flow before water immersion was measured, and then S1PC, SAC or purified water was orally administered to the rats. Two hours after the administration, the rats were immersed up to the xiphoid and below in water at 15° C. for 10 minutes, using a stainless-steel restraint cage. The tail skin blood flow after the water immersion stress was measured one hour after the end of water immersion stress.

2. Results

Results are summarized in Table 2. Measured values were given sd average±standard error.

Indications * and ** in Table 2 represent that a significant difference (*; p<0.05) was observed between the control group and the S1PC administration group, and that a significant difference (**; p<0.01) was observed between the S1PC administration group and the SAC administration group, as a result of comparing these groups one hour after the end of water immersion stress. The Bonferroni correction was used for examination.

TABLE 2

| Test Solution | Dose (mg/kg) | Tail skin blood flow (mL/min/100 g) | |
|---|---|---|---|
| | | Before water immersion stress | One hour after end of water immersion stress |
| Control group (purified water) | 0 | 3.61 ± 0.17 | 1.82 ± 0.15 |
| S1PC | 6.5 | 3.63 ± 0.16 | 2.59 ± 0.26 * |
| SAC | 6.5 | 3.58 ± 0.28 | 1.66 ± 0.19 ** |

*; p , 0.05, control group vs S1PC administration group,
**; p < 0.01, S1PC administration group vs SAC aministration group The group treated with S1PC by single oral administration two hours before the water immersion stress showed a significant effect of improving the tail skin blood flow with respect to the control group. In contrast, the group treated with SAC in the same dose by single oral administration did not show a significant effect of improving the tail skin blood flow. As a result of comparing between the S1PC group and the SAC group, the S1PC group provided a significantly higher value of tail skin blood flow, as compared with the SAC group.

The invention claimed is:

1. A method for improving cold sensitivity, stiff shoulder, backache, or swelling, the method comprising:
    administrating S-1-propenylcysteine or a salt thereof to a subject in need thereof,
    wherein a garlic extract obtained by extracting garlic in an ethanol aqueous solution for one month or more is not administered to the subject.

2. The method according to claim 1, wherein a rate of trans isomer of the S-1-propenylcysteine is from 50 to 100%, based on a total of trans isomer and cis isomer of the S-1-propenylcysteine.

3. The method according to claim 1, further comprising, prior to the administering:
    obtaining the S-1-propenylcysteine or a salt thereof from at least one Allium plant selected from the group consisting of garlic, onion, elephant garlic, Chinese chive, and spring onion.

4. The method according to claim 3, wherein the obtaining of the S-1-propenylcysteine or a salt thereof comprises:
    extracting the Allium plant in a 20 to 40% aqueous ethanol solution at 0 to 80° C. for one month or longer to obtain an extract;
    adsorbing the obtained extract to a cation exchange resin to obtain an adsorbate;
    eluting the adsorbate with a 0.1 to 3 N ammonia water to obtain an eluate;
    subjecting the eluate to a silica gel column chromatography and/or reverse phase column chromatography to obtain a target substance comprising the S-1-propenylcysteine or a salt thereof; and
    collecting the target substance.

5. The method according to claim 1, wherein a medicine containing the S-1-propenylcysteine or a salt thereof is administered to the subject.

6. The method according to claim 1, wherein a food containing the S-1-propenylcysteine or a salt thereof is administered to the subject.

7. A method of improving blood flow, the method comprising:
    administrating S-1-propenylcysteine or a salt thereof to a subject in need thereof,
    wherein a garlic extract obtained by extracting garlic in an ethanol aqueous solution for one month or more is not administered to the subject.

8. A method for improving cold sensitivity, stiff shoulder, backache, or swelling, the method comprising:
- extracting an Allium plant in a 10 to 50% aqueous ethanol solution at 0 to 80° C. for one month or longer to obtain an extract;
- adsorbing the obtained extract to a cation exchange resin to obtain an adsorbate;
- eluting the adsorbate with a 0.1 to 3 N ammonia water to obtain an eluate;
- subjecting the eluate to a silica gel column chromatography and/or reverse phase column chromatography to obtain S-1-propenylcysteine or a salt thereof;
- collecting the S-1-propenylcysteine or a salt thereof; and
- administrating the collected S-1-propenylcysteine or a salt thereof to a subject in need thereof.

9. The method according to claim 1, wherein only a composition consisting of the S-1-propenylcysteine or a salt thereof and water is administered to the subject.

* * * * *